United States Patent [19]

Bolesky et al.

[11] Patent Number: 4,479,271
[45] Date of Patent: Oct. 30, 1984

[54] PROSTHETIC DEVICE ADAPTED TO PROMOTE BONE/TISSUE INGROWTH

[75] Inventors: Richard C. Bolesky; Gene M. Farling; Barry L. Gold, all of Warsaw, Ind.

[73] Assignee: Zimmer, Inc., Warsaw, Ind.

[21] Appl. No.: 314,808

[22] Filed: Oct. 26, 1981

[51] Int. Cl.³ .......................... A61F 1/04; A61F 5/04
[52] U.S. Cl. ........................ 3/1.911; 3/1.91; 3/1.913; 128/92 C
[58] Field of Search ............... 264/263, 274; 3/1, 1.91, 3/1.911, 1.912, 1.913; 128/92 C, 92 CA

[56] References Cited

U.S. PATENT DOCUMENTS

| | | | |
|---|---|---|---|
| 3,293,106 | 12/1966 | Cocco et al. | 264/274 |
| 3,605,123 | 9/1971 | Hahn | 3/1 |
| 3,852,045 | 12/1974 | Wheeler et al. | 29/182 |
| 3,855,638 | 12/1974 | Pilliar | 3/1 |
| 3,906,550 | 9/1975 | Rostoker et al. | 3/1.912 |
| 4,068,379 | 1/1978 | Miller et al. | 32/14 A |
| 4,165,561 | 8/1979 | Miller et al. | 32/14 A |
| 4,202,055 | 5/1980 | Reiner et al. | 3/1.91 |
| 4,205,400 | 6/1980 | Shen et al. | 3/1.91 |
| 4,206,516 | 6/1980 | Pilliar | 3/1.9 |
| 4,207,627 | 6/1980 | Cloutier | 3/1.911 |

FOREIGN PATENT DOCUMENTS 13864 8/1980 European Pat. Off. ............ 3/1.911
1554454 10/1979 United Kingdom .

OTHER PUBLICATIONS

Shen et al., "Plastic Molded on Metal Endoskeleton to Form Top Half of Ankle Joint", Material Engineering, Nov. 1980.
"Multi-Radius Total Knee System," Zimmer, Brochure B-273-1 ©1980.
"The PCA ™ Total Knee System" Howmedica, Inc., Brochure H2027 ©1981.

Primary Examiner—Richard J. Apley
Assistant Examiner—David J. Isabella
Attorney, Agent, or Firm—Margaret L. Geringer

[57] ABSTRACT

This invention relates generally to the art of orthopaedic prostheses, and more particularly to the type of prosthesis which is adapted to promote the ingrowth of bone and/or tissue into the portion of the prosthesis surface in contact with the bone surface. The prosthesis is comprised of a bottom base layer of porous fiber metal material an intermediate metal reinforcing layer including at least one opening therein and a top non-metal surface which is molded to the base layer. The portion of the polyethylene layer that is in contact with the base layer penetrates into the interstices of the porous metal material, hence securing the non-metal layer to the porous metal base layer.

14 Claims, 10 Drawing Figures

PROSTHETIC DEVICE ADAPTED TO PROMOTE BONE/TISSUE INGROWTH

BACKGROUND OF THE INVENTION

This invention relates generally to the art of orthopaedic prostheses, and more particularly to the type of prosthesis which is adapted to promote the ingrowth of bone and/or tissue into the portion of the prosthesis surface in contact with the bone surface. Therefore, this type of prosthesis is generally not used with any bone cement or grouting material.

It is known in the art to adapt the portion of the prosthesis surface in contact with the bone to promote bone growth.

U.S. Pat. No. 3,855,638 (Robert M. Pilliar) describes a prosthetic device comprised of a solid metallic material substrate and a porous coating of metallic material adhered to and extending over a portion of the substrate surface. The porous coating described in this Pilliar patent consists of a plurality of small ball-shaped metallic particles which are bonded together at their points of contact with each other and said substrate to define a plurality of connected, interstitial pores uniformly distributed throughout the coating. This particular coating is described more fully in the Pilliar patent. It is an example of a type of porous coating which is adaptable or suitable for ingrowth of boney tissue into the porous coating.

U.S. Pat. No. 3,906,550 (Rostoker, et al) describes a prosthetic device which includes a porous fiber metal structure formed from the strands substantially sinusoidally shaped fiber strands. The points of contact between the fibers become metallurgically bonded by a sintering process. The particular fiber metal structure is described more fully in the Rostoker et al patent. This fiber metal structure provides at least a portion of the surface of the prosthetic device which is to be adjacent to the skeletal structure to enable bone and soft tissue growth into the fiber metal structure. Lines 35–44 in Column 3 of the Rostoker et al patent indicated a number of ways for securing the metal fiber structure to a solid metal portion. The preferred means is to metallurgically bond the fibers contacting the surface of a solid metal portion. Line 60 of Column 3 indicates that, in one particular embodiment of the invention, a wear insert is molded integrally with the fiber structure portion. The specification further indicates in lines 61–64 that the insert (which is not subject to bone ingrowth) can be held in place mechanically so that the insert can be subsequently removed and replaced if necessary. This statement seems to indicate that the wear insert is not actually molded to the fiber structure, by instead that the fiber structure is molded into shape about the already formed insert. The specification does not indicate what type of material the wear insert is. It is assumed that it could be any appropriate wear material appropriate for use in the body.

U.K. Patent No. 1,554,454 (Jack Chester Bokros) describes an implantable prosthetic device having a region of controlled porosity to promote the ingrowth of bone and/or tissue. This region is formed by a metal coil spring having a plurality of spaced apart points secured to the other points of the spring or substrate. It is indicated on page 2 of the specification, in lines 64 to 68, that the coil springs are preferably made from the same metal as the remainder of the prosthesis, however, in some cases, dissimilar metals are sometimes employed. Therefore, it appears that the metal coil spring portion of Bokros is intended for use with a metal substrate. It is indicated that the device is sintered in order for the portion of the spring in contact with the metal substrate to be bonded to the substrate, as well as for the touching loops of the helical springs to be sintered to one another at the points of contact.

It is also known in the art of prosthetic devices to reinforce non-metallic components (such as a polyethylene tibial knee component) by utilizing various types of metal retainers. This type of combination allows the non-metallic portion to be utilized as a bearing surface while the retainer is used for structural purposes. When any load is applied to the bearing surface, it is transmitted through the plastic to the metal retainer which distributes the load more evenly over the entire prosthesis. An example of one type of metal retainer is described in Jean-Marie Cloutier's U.S. Pat. No. 4,207,627.

OBJECTS OF THE INVENTION

A principle object of this invention is to provide a prosthetic device of the type which is adapted to promote the ingrowth of bone and/or tissue and which is designed for use with a non-metallic material.

Another object of this invention is to provide such a prosthesis having an effective means of securely and permanently interlocking the non-metallic material to the porous material.

A further object of the invention is to provide such a prosthetic device which may also be reinforced by an intermediate metal portion while still allowing for the secure attachment of the porous material to the non-metallic material.

SUMMARY OF THE INVENTION

The present invention accomplishes all of the above objects of invention. The prosthetic implant device of this invention is comprised of a bottom base layer of a porous metal material, and a top non-metal layer molded onto the base layer. At least a portion of the lower surface of the top non-metal layer is in contact with the upper surface of the bottom base layer such that the portion of the non-metal layer in contact with the upper base surface penetrates into the porous metal of the upper base surface, hence securing the porous material to the top layer's non-metal material. The upper surface of the non-metal layer is contoured appropriately for use as an articulating bearing surface. The geometrical shape of the device may be any suitable configuration for the particular joint component being replaced.

The device may include at least one porous metal stem protruding from the lower base surface of the bottom layer. The lower base surface and the outer exposed surface of the protruding stems are adapted to be in direct contact with the prepared bone surface to promote the ingrowth of bone and/or tissue.

The prosthetic device may further include an intermediate metal reinforcing layer disposed between the bottom base layer and the top non-metal layer. The reinforcing layer includes at least one opening there through, allowing the non-metal material of the top layer (such as ultra high molecular weight polyethylene) to fill any such opening, and hence contact and penetrate the upper porous surface of the porous base layer at the open area.

BRIEF DESCRIPTION OF THE DRAWINGS

In order that the principles of the present invention may be readily understood, various embodiments of the present invention will be described with reference to the accompanying drawings, which form part of the original disclosure of this application, and wherein.

DETAILED DESCRIPTION OF THE INVENTION

FIGS. 1 through 10 illustrate various embodiments of the invention. The invention will be described with reference to a tibial knee prosthesis component and a patellar component. It is understood that the principles of the invention can be adapted to other joint components where it is desirable to have a non-metallic bearing surface and also provide a means for promoting bone ingrowth.

Figures 1, 2:
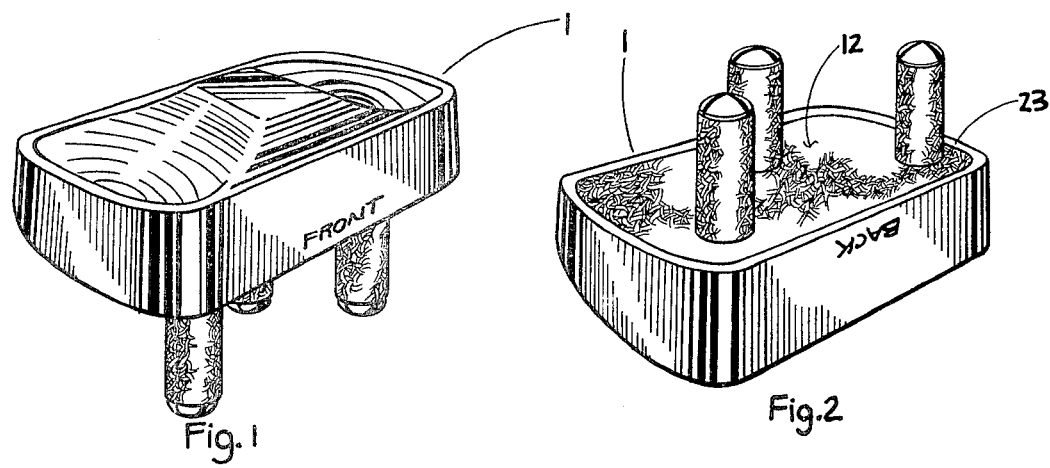
FIG. 1 illustrates a perspective view of a particular embodiment of a tibial knee component.
FIG. 2 illustrates a perspective view of the tibial knee component of FIG. 1, as viewed from the underneath side.
Figure 3:
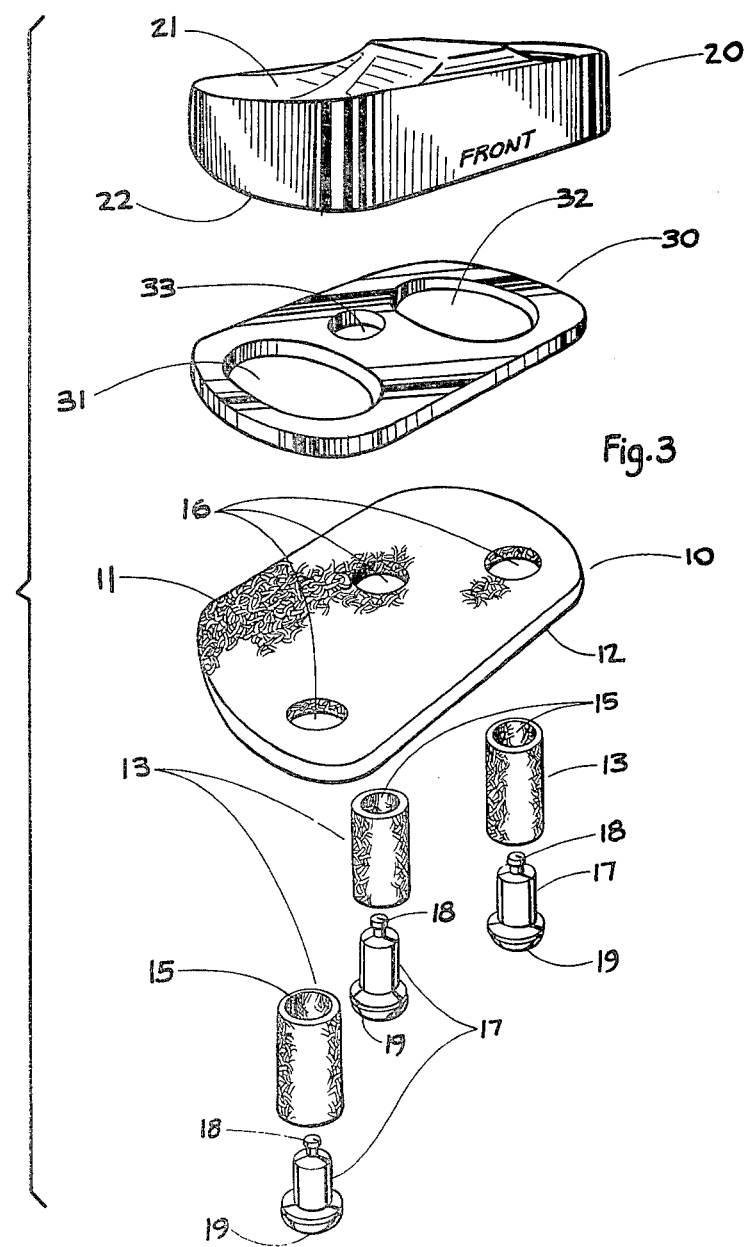
FIG. 3 illustrates an exploded perspective view of the tibial knee component of FIG. 1.

FIGS. 1 through 8 illustrate a tibial knee component. The tibial component 1, as illustrated in FIG. 3, is comprised of a bottom base layer 10 of a porous metal material and a top non-metal layer 20 which is molded onto the base layer 10. The bottom base layer 10 includes an upper base surface 11 and a lower base surface 12. The top non-metal layer includes an upper non-metal surface 21 and a lower non-metal surface 22. At least a portion of the lower non-metal surface 22 is in contact with the upper base surface 11 such that said portion of the non-metal layer in contact with the upper base surface 11 penetrates into the porous metal material of the upper base surface 11.

The porous material of the base layer 10 is preferably a porous fiber mesh material, such as the type described in Rostoker, et al's U.S. Pat. No. 3,906,550. It is understood for the purposes of this invention that the type of fiber mesh used could be other than the specific type described in this patent, but that the type described in the patent is merely an example of the type of fiber mesh which is suitable. The fiber mesh must be porous throughout to allow the non-metallic material, such as high molecular weight polyethylene, to penetrate the pores on the upper base surface 11, and to allow for suitable bone/tissue ingrowth on the portion of the mesh in direct contact with the bone or tissue interface. It is also understood that other suitable porous metal materials could be used other than the fiber mesh, but the preferred embodiment of the invention will be described and illustrated with reference to this type of porous fiber metal mesh material. The metal mesh may be made of commercially pure titanium, although other suitable materials may also be used.

The fiber mesh material can be molded or compressed into the desired shape. The geometry of the porous layer may be of any suitable geometry for the particular body portion which is being replaced. The important factor is ensuring that the portion of the bone which will be in contact with the fiber mesh portion of the prosthesis is shaped and contoured to reflect the shape and contour of the portion of the prosthesis which will be contacting the bone. It is important that this interface of the prosthesis with the bone/tissue portion conforms with each other to provide contact between the bone/tissue and porous portion to ensure good bone/tissue ingrowth. Therefore, if the lower base surface 12 is flat with three protruding stems 13 as shown in FIG. 3 for the particular tibial embodiment illustrated, the mating bone portion should also be flat with three corresponding openings sized to securely fit about the stems 13.

The upper non-metal surface 21 is the articulating surface, or the surface which may mate with another prosthesis component. The configuration of this surface 21 may be of any suitable geometry for the particular joint portion which is being replaced. The non-metal material may be of any suitable biocompatible material, such as ultra-high-molecular-weight-polyethylene.

The tibial component illustrated in FIGS. 1-8 may further include at least one porous metal stem 13 protruding from the lower base surface 12. The embodiment of the tibial component 1 illustrated, utilizes three protruding stems 13, as shown. Also, if more than one stem 13 is used, they may or may not be the same length. The lower base surface 12 and the outer (exposed) surface of the three protruding stems 13 are the surfaces which are adapted to be in direct contact with the prepared bone/tissue surface. The shape of the stems 13, as illustrated, are cylindrical. This is merely a convenient, simple shape to use. Any practical shape (triangular, etc.) may be used as long as the bone surface is prepared to match with a corresponding shape.

The stems 13 may further include a bore 15 extending from the distal end of the stem through to the upper base surface 11. The bores 15 allow the polyethylene to flow into the bores 15 as the polyethylene layer 20 is molded onto the base layer 10. This further secures the polyethylene layer 20 to the bottom base layer 10 and to the stems 13 because the polyethylene further flows into the porous surface on the interior surface of the bore 15. The polyethylene may penetrate into the fiber mesh material approximately one millimeter. The fiber mesh portion is preferably thick enough to allow the 1 mm penetration of the polyethylene on the surface of the mesh contacting the polyethylene, as well as allowing for up to at least one to two millimeters of penetration for the bone/tissue ingrowth on the surface of the porous material contacting the bone/tissue surface. It is pointed out that the cross-sectional views (FIG. 5, 8, and 9) do not illustrate the penetration of the polyethylene into the porous layer, as it was felt that this would make the drawings confusing. It was felt that the concept of the penetration could be understood through the written description.

The stems 13 may further include a stud 14 inserted in the distal opening of the bore 15. The stud 14 may be of a solid metal biocompatible material. The head portion 19 of the stud 14 is rounded and smooth and helps to guide the stems 13 into the corresponding holes which are prepared for them in the tibial bone. The studs 14 also help to reinforce the stems 13. The studs preferably do not extend further than the lower base surface 12 so that if the tibial component has to be removed for some reason, the component can be removed with a chisel. The chisel can only go through the fiber mesh portion and the polyethylene. The chisel would be driven along the underneath side of lower base surface and through the portion of the stems 13 interfacing with the lower base surface 12. The stems 13 (including the studs) could then be extracted with a hollow mill.

The studs 14 may also include a neck portion 17 and a lip portion 18. This helps to further interlock the stud 14 with the polyethylene of the top layer 20 which flows into the bore 15 of the stem 13.

Figure 4:
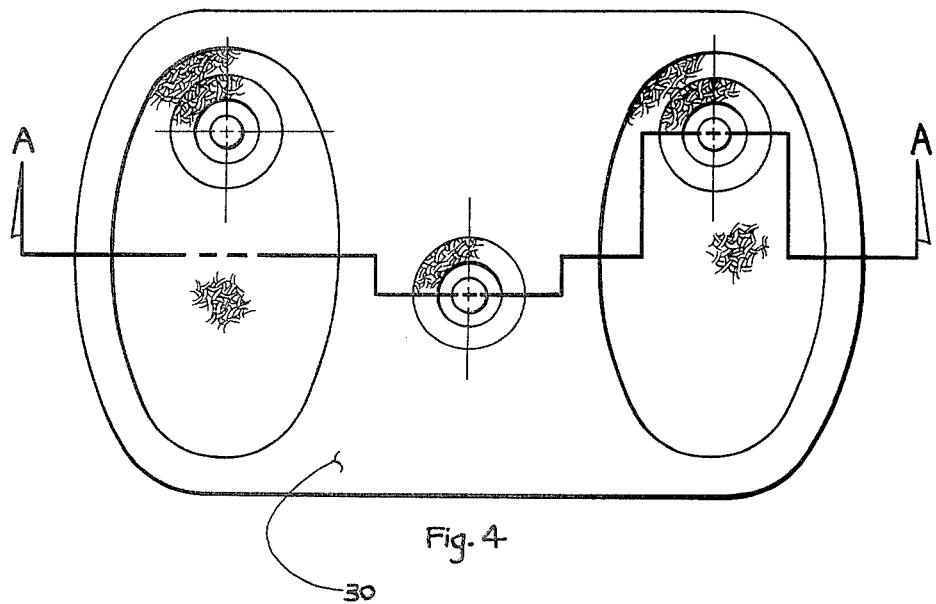
FIG. 4 illustrates a top view of the metal reinforcing layer and the porous metal portion of the tibial knee component of FIG. 3.
Figure 5:
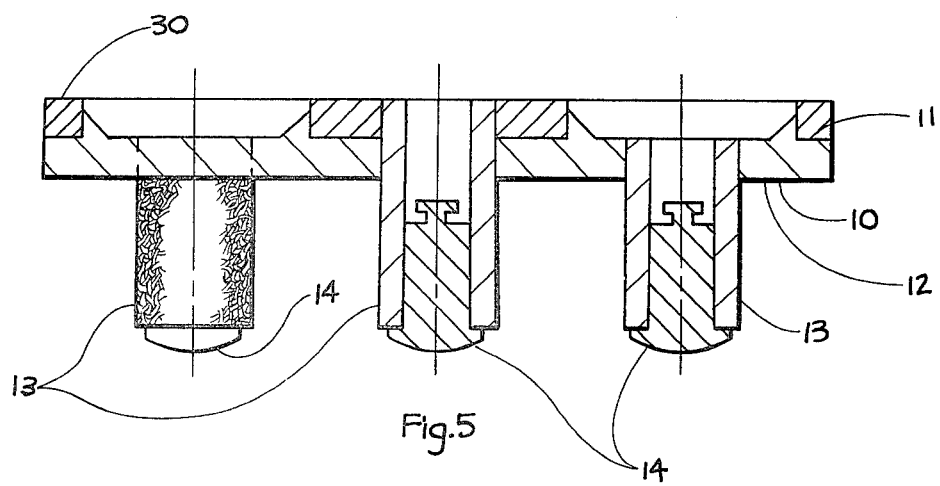
FIG. 5 illustrates a sectional view of the tibial knee component taken along lines A—A of FIG. 4.

As illustrated in FIGS. 3, 4, and 5, the tibial component 1 may further include an intermediate metal reinforcing layer disposed between the base layer 10 and the top layer 20. The reinforcing layer 30 must include at least one opening therethrough, for allowing the polyethylene of the top layer 20 to fill the opening and hence contact and penetrate the porous material of the base layer 10 to form an interlock of the polyethylene layer onto the bottom base layer 10.

In the embodiment of the tibial component 1 illustrated in FIGS. 3, 4, and 5, the tibial component 1 includes a first opening 31 and a second opening 32. The first opening 31 is located on the right portion of the tibial component 1 and the second opening 32 is located on the left portion of the tibial component 1. The first and second openings are each positioned over a stem, thus allowing the polyethylene to be able to flow into these stems when the polyethylene is molded onto the combination of the reinforcing plate 30 and base layer 10. The first and second openings 31 and 32 are substantially oval shaped and are positioned such that they lie beneath the two concave articulating surfaces of the upper polyethylene surface 21. The particular articulating surface of the tibial embodiment illustrated is of the type having two concave articulating portions for mating with a femoral component having two corresponding convex articulating portions. Many styles of knees use this type of articulating surface which corresponds generally to the condyle portions of the human femur and tibia. The first and second openings 31 and 32 are therefore positioned underneath the portion of the tibial articulating surface which will receive the most wear. Therefore, the openings 31 and 32 also allow the polyethylene at these positions to be thicker for wear purposes.

The tibial component 1 illustrated in FIGS. 3, 4, and 5 further includes a third opening 33 in the reinforcing layer 30. The third opening is much smaller in comparison to the first and second openings 31 and 32. The third opening is located in the central portion of the metal reinforcing layer 30. The third opening 33, in the embodiment shown, is also positioned over a stem 13 to allow the polyethylene to flow into the bore 15 in the stem 13.

When the polyethylene layer 20 of the tibial component 1 is molded onto the porous base layer 10, without the inclusion of a metal reinforcing layer 30, as the molded polyethylene (which has penetrated into the porous layer 10) cools down, it tends to shrink which can cause some bowing in the porous base layer 10 which is not desirable. The reinforcing layer 30 prevents this bowing from occurring. The metal reinforcing layer 30 also gives added strength to the tibial component which is a load bearing prosthetic component.

The preferred process of manufacturing the particular tibial component 1 illustrated in FIGS. 1 to 5 is as follows:

The porous base layer of fiber mesh is molded or compressed into the desired shape. In the particular embodiment shown, the base layer 10 is a substantially flat pad having a substantially flat upper and lower surface 11 and 12. The base layer 10 has a front, back, and two connecting sides. The base layer 10 includes three holes 16 which are for the three stems 13. The three porous fiber mesh stems 13, each including a bore 15 therethrough, are also molded and compressed into shape. (The base layer 10 and stems could be molded in one piece if desirable.) The stems 13 are force fit into the holes 16 in the base layer. The end face of the stems 13 which are to be positioned beneath the openings 31 and 32 in the reinforcing layer 30 are flush with the upper base surface 11. The end of the stem 13 which is positioned in line with the opening 33 in the reinforcing layer 30 is flush with the top surface of the reinforcing layer 30 which is positioned on the upper base surface 11. The studs 14 are force fit into the protruding ends of each stem 13.

This whole combination of the porous bottom layer 10, the three porous stems 13 with metal studs 14, and the metal reinforcing layer 30 are all sintered. The sintering process creates metallurgical bonds at the points of contact of the fibers of the porous mesh material as well as creates metallurgical bonds at the points of contact between the fibers and the metal studs 14 between the fibers and the metal reinforcing layer 30.

This combination is then placed in an appropriate mold for molding the polyethylene layer 20 onto the intermediate and bottom layers 30 and 10. The polyethylene flows through the openings in the reinforcing layer 30 and flows into the bores 15 in the stems 13. The polyethylene penetrates the exposed surfaces of the porous fiber mesh material on the inner surfaces of the bores 15 and the exposed portions of the upper porous base layer 11 interlocking the polyethylene to the porous mesh material. The polyethylene portion may include a ridge 23 about its periphery which extends down from the polyethylene layer to and flush with the lower base surface 12. This is illustrated more clearly in FIG. 8.

Figure 6:
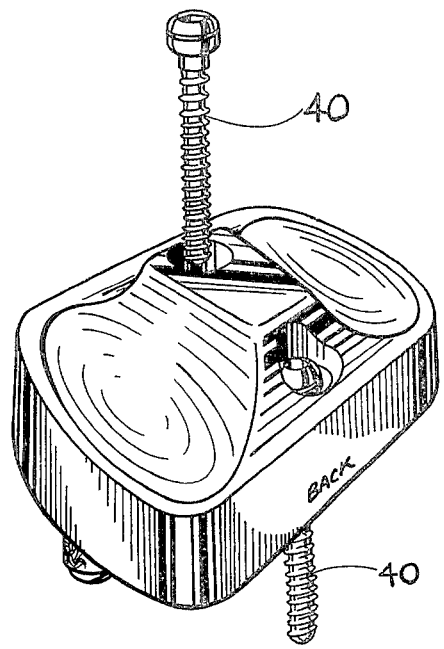
FIG. 6 illustrates a perspective view of an alternate embodiment of the tibial knee component.
Figure 8:
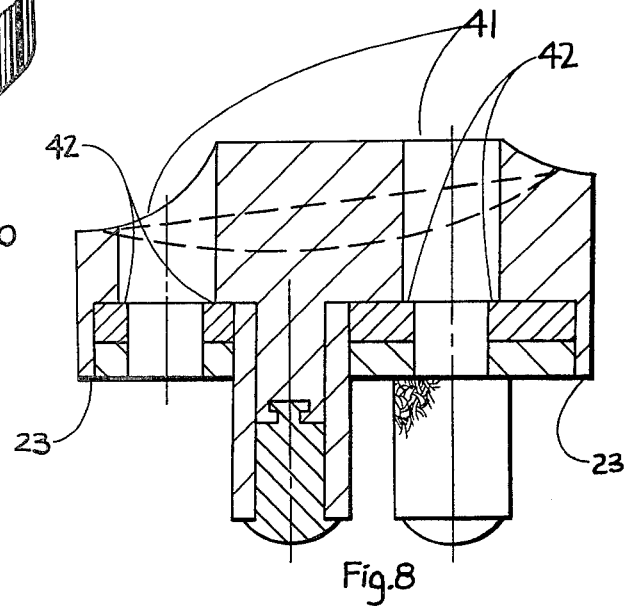
FIG. 8 illustrates a sectional view of the tibial knee component taken along lines B—B of FIG. 7.
Figure 7:
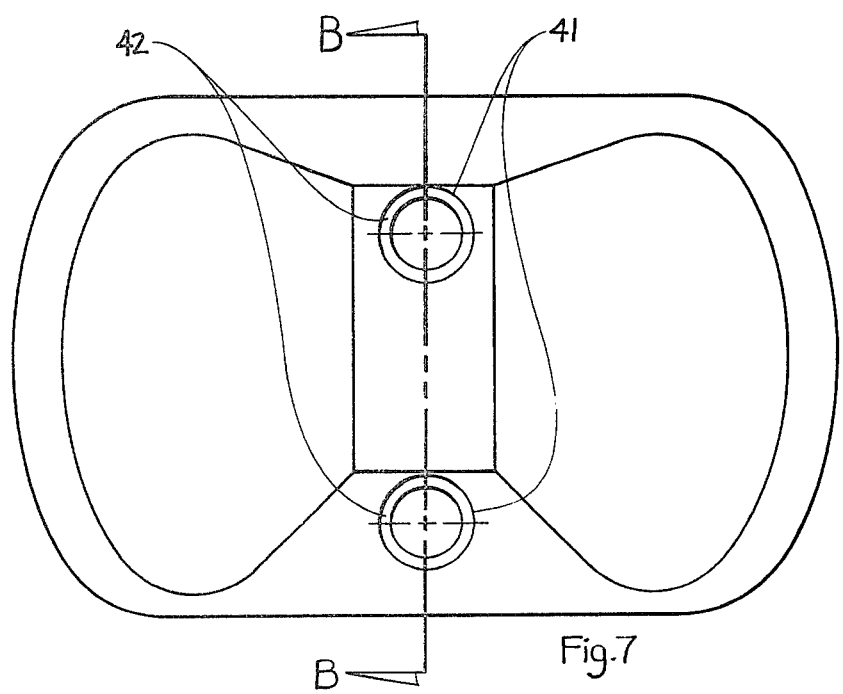
FIG. 7 illustrates a top view of the tibial knee component of FIG. 6.

FIGS. 6 and 7 illustrate a tibial component made in accordance with this invention which further includes the use of two fixation holes 41 which extend from the upper polyethylene surface 21 through to the lower base surface 12. The fixation holes 41 are adapted to receive a bone screw 40 for further securing of the tibial prosthesis to the tibial bone. Even if the fixation holes 41 are included in a device, the screws 40 may or may not be used depending upon the preference of the procedure used. The screw holes are located on a non-articulating portion of the upper polyethylene surface 21, therefore they don't interfere with the articulating motion of the tibial component 1 with a mating prosthesis. The portion of the fixation hole 41 going through the polyethylene layer 20 is of a larger diameter than the portion of the hole 41 through the reinforcing and base layer 30 and 10, as illustrated in FIG. 8. This provides a ledge 42 for the screw head to seat against. Any suitable bone screw may be used.

The use of an additional fixation means such as the fixation screws 40, in association with a prosthetic device adapted to promote the ingrowth of bone and/or tissue is not new in and of itself. It is merely a further adaptation which may be used with the present invention, if desirable.

Figures 9, 10:
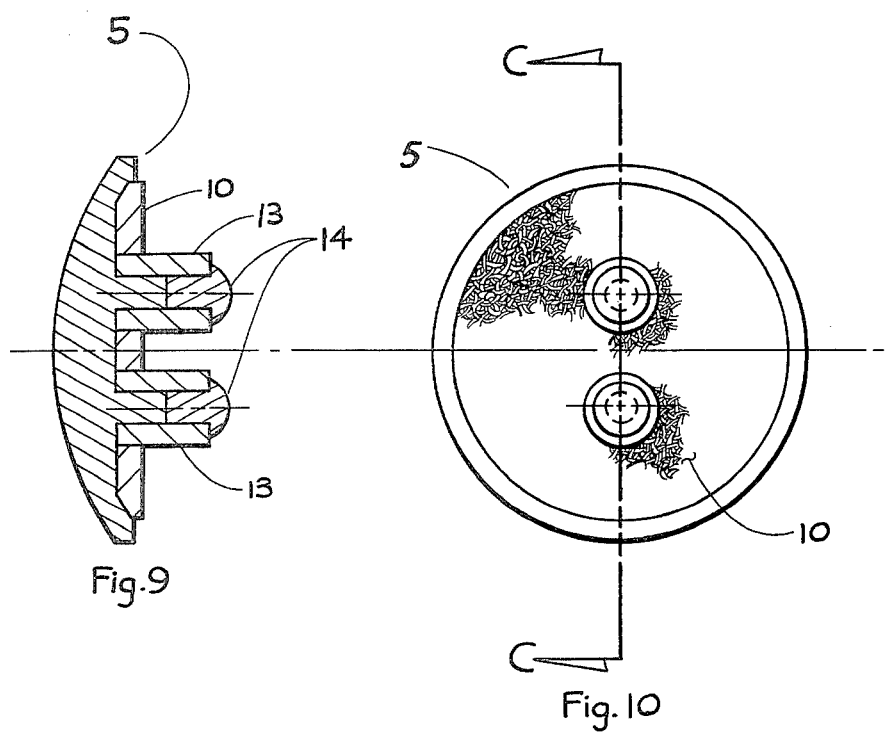
FIG. 9 illustrates a sectional view of a patellar component for a knee taken along lines C—C of FIG. 10.
FIG. 10 illustrates a bottom view of the patellar component of FIG. 9.

FIGS. 9 and 10 illustrate the present invention used in association with a patellar prosthesis 5. Again, the geometrical design may be any suitable configuration for a particular patellar prosthesis. The patellar prosthesis 5 illustrated in FIG. 9 and 10 is comprised of a bottom porous metal base layer 10 with two porous metal stems 13 protruding from the lower base surface 12. The stems 13 each include a bore 15 therethrough. The end face of the stems 13 are flush with the upper base surface 11. The protruding ends of the stems each include a metal stud 14. The metal studs 14 illustrated for the patellar prosthesis 5 do not include the neck 17 and lip 18 portion.

The porous base layer 18 the of patella 5 of the embodiment illustrated is substantially flat and round in shape. The top non-metal layer 20 is molded to the porous base 10 and porous stems 31, as shown, such that the non-metal material penetrates the pores of the porous material interlocking the top layer 20 to the porous portion. The contour of the upper non-metal surface 21 is the patellar articulating surface. This surface 21 may be contoured to mate with the appropriate mating knee component. The non-metal layer 20 for the patella 5 may also include a ridge 23 about the peripheral edge which extends around the outer edge of the porous metal layer 10.

The porous layer 10 and porous stems 13, as illustrated, are also made of an appropriate porous fiber mesh material for bone ingrowth. The fibers are molded and compressed into shape and then sintered creating metallurgical bonds at the points of contact of the fibers of the porous mesh material. The non-metal layer 20 is then molded onto the porous metal portion.

The particular embodiment of the patellar prosthesis 5 illustrated does not include a metal reinforcing layer. The part is relatively small, and the addition of a small metal reinforcing layer would tend to make the manufacture more difficult. Also, since the particular embodiment illustrated utilizes a circular base layer 10, when the non-metal, such as polythylene, is molded onto the porous material, as the polyethylene cools and shrinks, the shrink is uniform about the circular shape, and therefore, the bowing is not a problem.

It is understood that the principles of this invention can be used in combination with other prosthetic components where it is desirable to have a non-metal bearing surface used in conjunction with a porous material adapted for bone/tissue ingrowth. It is also understood that any appropriate articulating surface may be used, as well as a wide variety of adaptable prosthesis design structures. While this invention has been described and exemplified in terms of a particularly advantageous embodiment, those skilled in the art can appreciate that modifications and variations can be made without departing from the spirit and scope of this invention.

We claim:

1. A tibial component for a knee joint prosthesis comprising:
   (a) a bottom base layer of a porous metal material having an upper base surface, and a lower base surface, defining a thickness of porous material therebetween, said lower base surface adapted to be in direct contact with a prepared bone surface to promote the ingrowth of bone and/or tissue into the porous material, and
   (b) a top non-metal layer molded onto the upper base surface of the bottom base layer and wherein said non-metal layer has an upper non-metal surface and a lower non-metal surface, wherein said upper non-metal surface is contoured appropriately for use as an articulating bearing surface, and wherein at least a portion of the lower non-metal surface is in direct contact with the upper base surface wherein said portion of the non-metal layer in contact with the upper base surface penetrates into the porous metal of the upper base surface to secure said non-metal layer to the porous base layer, said non-metal material penetrating only partially through the thickness of porous material, leaving the lower portion of the porous layer free to allow for the ingrowth of bone and/or tissue in through the porous lower base surface, and
   (c) and intermediate metal reinforcing layer disposed between the bottom base layer and the top non-metal layer wherein said reinforcing layer includes at least one opening, therefore allowing the non-metal material to the top layer to fill the at least one opening, and hence contact and penetrate the porous surface of the porous bottom base layer at the opening, and
   (d) at least one porous metal stem protruding from the lower base surface of the bottom base layer, wherein said outer surface of the protruding stems is adapted to be in direct contact with the prepared bone surface to promote the ingrowth of bone and/or tissue, and wherein each protruding porous metal stem includes a bore therethrough which extends from the distal end of the stem through to the upper surface of the bottom base layer.

2. A tibial component as described in claim 1 wherein each stem has a stud inserted in the distal opening of the bore.

3. A tibial component as described in claim 2 wherein the non-metal layer further extends into the proximal opening of the bore in each stem further securing the non-metal layer to the base layer.

4. A tibial component as described in claim 1 wherein the bottom base layer is at least 2 mm thick.

5. A tibial component as described in claim 1 wherein said component includes three protruding stems extending from the lower base surface of the base layer.

6. A tibial component as described in claim 1 wherein the at least one opening in the metal reinforcing layer is positioned to allow the non-metal material to additionally flow into the bore portion of the at least one porous metal stem.

7. A tibial component as described in claim 1 wherein said at least one opening in the metal reinforcing layer is comprised of a first opening on the right portion of the metal reinforcing layer and a second opening on the left portion of the metal reinforcing layer.

8. A tibial component as described in claim 2 wherein said metal reinforcing layer further includes a third, but relatively smaller, opening in the central portion of the reinforcing layer.

9. A tibial component as described in claim 1 wherein said tibial component further includes at least one fixation bore therethrough on the non-articulating portion of the upper non-metal surface, said fixation bore extending from the upper non-metal surface through to the lower base surface, said at least one fixation bore adapted to receive a bone screw for further securing the tibial prosthesis to the tibial bone.

10. A tibial component as described in claim 1 wherein the top non-metal layer has a ridge about its periphery which extends down from the non-metal layer to the lower surface of the base layer and is flush with the lower base layer surface.

11. A tibial component as described in claim 1 wherein said non-metal material is ultra-high-molecular-weight polyethylene.

12. A prosthetic implant device comprising:
(a) a bottom base layer of a porous metal material having an upper base surface, and a lower base surface, defining a thickness of porous material therebetween, said lower base surface adapted to be in direct contact with a prepared bone surface to promote the ingrowth of bone and/or tissue into the porous material and
(b) a top non-metal layer molded onto the upper base surface of the bottom base layer and wherein said non-metal layer has an upper non-metal surface and a lower non-metal surface, wherein said upper non-metal surface in contoured appropriately for use as an articulating bearing surface, and wherein at least a portion of the lower non-metal surface is in direct contact with the upper base surface wherein said portion of the non-metal layer in contact with the upper base surface penetrates into the porous metal of the upper base surface to secure said non-metal layer to the porous base layer, said non-metal material penetrating only partially through the thickness of the porous layer, leaving the lower portion of the porous layer free to allow for the ingrowth of bone and/or tissue in through the porous lower base surface, and
(c) an intermediate metal reinforcing layer disposed between the bottom base layer and the top non-metal layer wherein said reinforcing layer includes at least one opening, therefore allowing the non-metal material of the top layer to fill the at least one opening, and hence contact and penetrate the porous surface of the bottom base layer at the opening.

13. A prosthetic device as described in claim 12 wherein said device further includes at least one porous metal stem protruding from the lower base surface of the bottom base layer, wherein said outer surface of the protruding stems is adapted to be in direct contact with the prepared bone surface to promote the ingrowth of bone and/or tissue.

14. A prosthetic device as described in claims 1 or 12 wherein the porous metal material is a porous fiber mesh material.

* * * * *